United States Patent
Balduf

(10) Patent No.: US 8,829,235 B2
(45) Date of Patent: Sep. 9, 2014

(54) PROCESS FOR PREPARATION OF METHYL METHACRYLATE BY ESTERIFICATION DURING OXIDATION

(75) Inventor: Torsten Balduf, Pfungstadt (DE)

(73) Assignee: Evonk Röhm GmbH, Darmstadt (DE)

( * ) Notice: Subject to any disclaimer, the term of this patent is extended or adjusted under 35 U.S.C. 154(b) by 218 days.

(21) Appl. No.: 12/598,438

(22) PCT Filed: Feb. 25, 2008

(86) PCT No.: PCT/EP2008/052225
§ 371 (c)(1),
(2), (4) Date: Nov. 2, 2009

(87) PCT Pub. No.: WO2008/145417
PCT Pub. Date: Dec. 4, 2008

(65) Prior Publication Data
US 2010/0130648 A1    May 27, 2010

(30) Foreign Application Priority Data

May 25, 2007    (EP) .................................... 07010480

(51) Int. Cl.
| | |
|---|---|
| C07C 51/245 | (2006.01) |
| C07C 51/16 | (2006.01) |
| C07C 51/23 | (2006.01) |
| C07C 67/03 | (2006.01) |
| C07C 67/08 | (2006.01) |
| C07C 51/25 | (2006.01) |
| C07C 67/39 | (2006.01) |

(52) U.S. Cl.
CPC .............. *C07C 51/252* (2013.01); *C07C 51/23* (2013.01); *C07C 67/03* (2013.01); *C07C 67/08* (2013.01); *C07C 67/39* (2013.01)
USPC ......................................... 562/532; 562/544

(58) Field of Classification Search
None
See application file for complete search history.

(56) References Cited

U.S. PATENT DOCUMENTS

| | | | | |
|---|---|---|---|---|
| 3,758,551 A | * | 9/1973 | Murib et al. .................. | 560/208 |
| 3,925,463 A | * | 12/1975 | Ferlazzo et al. .............. | 560/208 |

(Continued)

FOREIGN PATENT DOCUMENTS

| | | |
|---|---|---|
| AU | 5848380 | 11/1980 |
| DE | 31 06 945 A1 | 12/1981 |

(Continued)

OTHER PUBLICATIONS

U.S. Appl. No. 12/598,513, filed Nov. 2, 2009, Balduf.

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to a process for preparation of methacrylic acid, comprising the steps: a) providing a feed composition comprising a main compound selected from isobutylene and tert-butyl alcohol and at least one co-compound selected from the group consisting of methanol, dimethyl ether and formaldehyde; b) subjecting the feed composition provided in step a) with at least a first part of said at least one co-compound to a catalytic reaction zone and obtaining an oxidation phase comprising methyl methacrylate and methacrylic acid. The invention also relates a process for preparation of methyl methacrylate, further comprising the step of: c) esterification of at least a part of the oxidation phase obtained in step b), to an apparatus for preparation of methacrylic acid, to an apparatus for preparation of methyl methacrylate, to a process carried out in the apparatus, to methacrylic acid, to methyl methacrylate, to methacrylate esters, to a process for preparation of a polymer comprising at least one methacrylic acid, methyl methacrylate and/or methacrylate ester monomer unit, to a polymer comprising at least one methacrylic acid, methyl methacrylate and/or methacrylate ester monomer, to a process for preparation of a composition, to a composition, to chemical products, and to the use of at least one of methacrylic acid, methyl methacrylate, methacrylate ester, a polymer and/or a composition in chemical products.

21 Claims, 1 Drawing Sheet

(56) References Cited

U.S. PATENT DOCUMENTS

| | | | |
|---|---|---|---|
| 4,014,925 A * | 3/1977 | Ferlazzo et al. | 560/208 |
| 4,060,545 A * | 11/1977 | Miller et al. | 560/208 |
| 4,147,721 A | 4/1979 | Leacock | |
| 4,147,884 A | 4/1979 | Sheng et al. | |
| 4,356,316 A | 10/1982 | Aoshima et al. | |
| 4,962,133 A | 10/1990 | Chromecek et al. | |
| 5,670,702 A * | 9/1997 | Jackson et al. | 560/208 |
| 6,107,515 A * | 8/2000 | Yamaguchi et al. | 560/261 |
| 6,214,942 B1 | 4/2001 | Siol et al. | |
| 6,265,028 B1 * | 7/2001 | Zhao et al. | 427/372.2 |
| 2002/0188151 A1 * | 12/2002 | Inoue et al. | 560/205 |
| 2003/0069327 A1 | 4/2003 | Walz et al. | |
| 2003/0216587 A1 | 11/2003 | Au et al. | |
| 2006/0009589 A1 | 1/2006 | Haering et al. | |
| 2006/0135833 A1 * | 6/2006 | Malzkorn et al. | 585/638 |

FOREIGN PATENT DOCUMENTS

| | | |
|---|---|---|
| DE | 102 33 685 | 2/2004 |
| EP | 0 417 606 | 4/1995 |
| EP | 0 886 658 | 12/1998 |
| EP | 0 970 993 | 1/2000 |
| EP | 1 254 887 | 11/2002 |
| JP | 55151533 | * 11/1980 |
| JP | 57-209233 | 12/1982 |
| JP | 60-60111 | 4/1985 |
| JP | 5-179054 | 7/1993 |
| JP | 10-120861 | 5/1998 |
| JP | 2001-64471 | 3/2001 |
| JP | 2003-26633 | 1/2003 |
| NL | 8002829 | 11/1980 |
| TW | I1237634 | 8/2005 |
| TW | 200617172 A | 6/2006 |

OTHER PUBLICATIONS

U.S. Appl. No. 12/597,540, filed Oct. 26, 2009, Balduf.
European Office Action issued Aug. 8, 2011, in Patent Application No. 07 010 480.7.
Chinese Office Action issued Jun. 6, 2012 in connection with Chinese Patent Application No. 200710129065.6, filed Jul. 11, 2007.
Office Action issued Jan. 18, 2013 in Japanese Application No. 2010-509756 (English Translation).
U.S. Appl. No. 14/240,547, filed Feb. 24, 2014, Balduf, et al.
U.S. Appl. No. 14/342,116, filed Feb. 28, 2014, Schaefer, et al.
Office Action issued Sep. 23, 2013, in Taiwanese Patent Application No. 097118761 filed May 21, 2008 (with English translation).

* cited by examiner

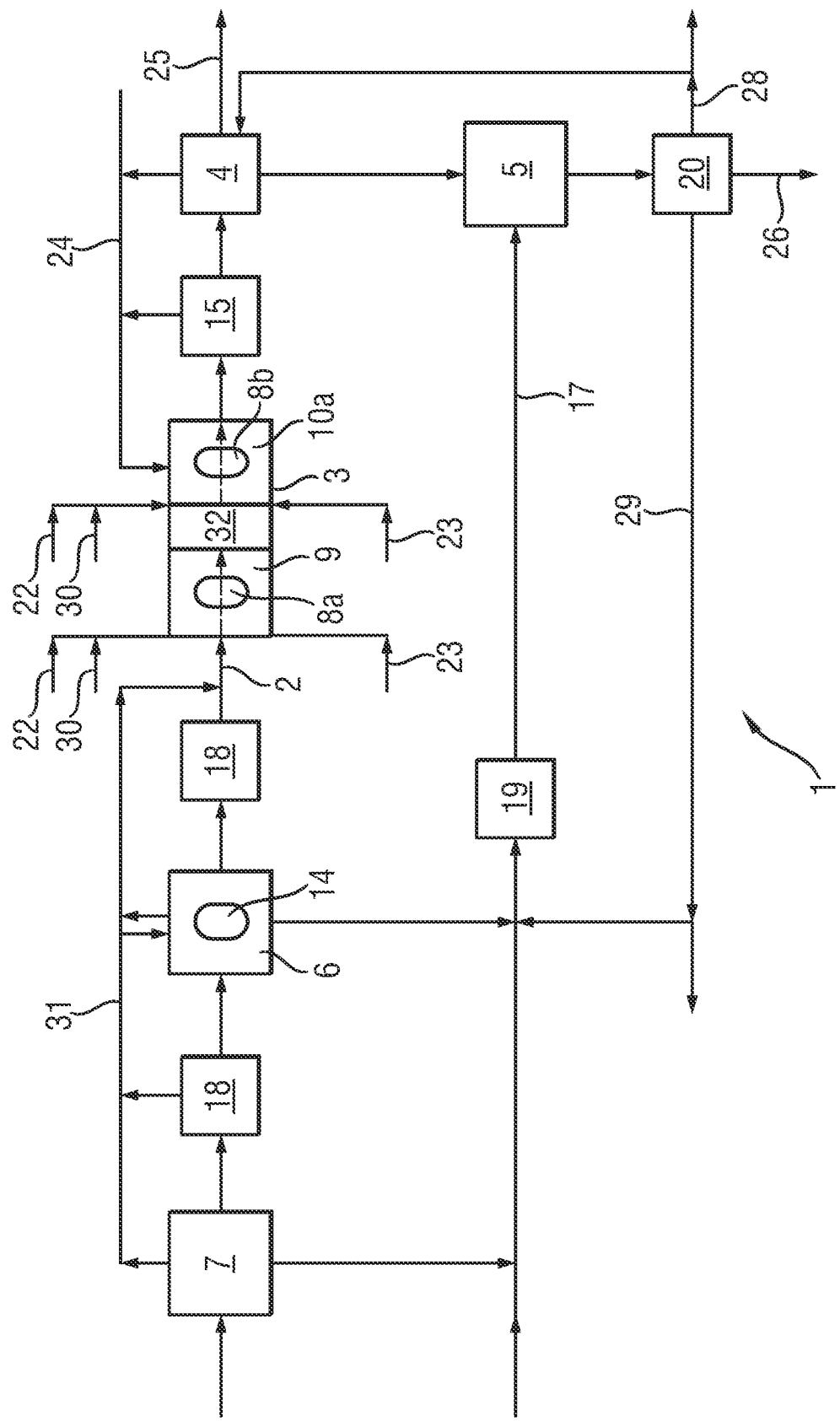

PROCESS FOR PREPARATION OF METHYL METHACRYLATE BY ESTERIFICATION DURING OXIDATION

The invention relates in general to a process for production of methacrylic acid, to a process for production of methyl methacrylate, to an apparatus for production of methacrylic acid, to an apparatus for production of methyl methacrylate, to a process carried out in the apparatus, to methacrylic acid obtainable by the process, to methyl methacrylate obtainable by the process, to methacrylate esters, to a process for preparation of a polymer comprising at least one methacrylic acid, methyl methacrylate or methacrylate ester monomer unit, to a polymer comprising at least one methacrylic acid, methyl methacrylate and/or methacrylate ester monomer unit, to a process for preparation of a composition comprising at least one of methacrylic acid, methyl methacrylate, methacrylate ester and a polymer, to a composition, to chemical products comprising at least one of methacrylic acid, methyl methacrylate, methacrylate ester, a polymer and/or a composition, and to the use of at least one of methacrylic acid, methyl methacrylate, methacrylate ester, a polymer and/or a composition in chemical products.

Methacrylic acid (MAA) and polymethacrylic acid (PMAA) are important industrial products with applications in, for example, thickening agents, suspending agents, flocculants, resins and absorbent materials, among other applications. A significant proportion of industrially produced MAA is, however, used in the production of its esters, in particular of methyl methacrylate and polymethyl methacrylate, as well as special esters for specific applications.

Methyl methacrylate (MMA) is a valuable industrial product with estimated current worldwide production of 3.3 million metric tons per year. It is principally used in the production of polymethyl methacrylate (PMMA) acrylic plastics. PMMA materials have high transparency, weathering stability and resistance to scratching, as well as being easily moulded, light and having high breaking strength. They are used, among other applications, in automobile and transportation systems, in optics and communications, in medical technology and in construction and lighting.

Other important applications are in the production of copolymers such as the copolymer methyl methacrylate-butadiene-styrene (MBS), which is used as a modifier for PVC; in paints and varnishes such as waterborne coatings, for example latex house paint; in adhesives; and more recently in plates that keep light spread evenly across LCD computer and TV screens, for example in flat screens, and in contact lenses. Methyl methacrylate is also used in preparation of corrosion casts of anatomical organs, such as coronary arteries of the heart.

Special methacrylate ester derivatives, for example, of alkyl and aryl alcohols, hydroxyalcohols, polyethylene glycols, quaternary ammonium derivatives and aminoalcohols, among others, have applications in, for example, contact lenses, coatings, drug delivery, controlled release of active substances, adhesives, lubricants, flow improvers, compatibility agents for polymer blends, bonding agents, food packaging, lacquers and PVC-free underseal compounds for automobile manufacture.

Various processes are known in the art for preparing methyl methacrylate, such as those based on hydrolysis of acrylonitrile or on the reaction of acetylene, carbon monoxide and an alcohol in the presence of a nickel carbonyl complex. An acetone cyanohydrin (ACH) route, with acetone and hydrogen cyanide as raw materials, is also applied. A disadvantage of these routes is the extremely high toxicity of nickel carbonyl and acetone cyanohydrin. A preferred route is the esterification of methacrylic acid with methanol.

According to a widely used industrial process for preparation of methacrylic acid, isobutylene or TBA is oxidised on suitable catalysts, first to methacrolein and then further to methacrylic acid. Either the methacrolein or the methacrylic acid is then esterified with methanol, in the case of methacrolein in an oxyesterification reaction, to form the desired methacrylate. The isobutylene used in this process is often obtained by splitting of methyl tert-butyl ether (MTBE) to provide isobutylene and methanol, together with side products including dimethyl ether and tert-butyl alcohol (TBA), as well as unreacted MTBE. Isobutylene can also be obtained from splitting of ethyl tert-butyl ether (ETBE) to afford principally isobutylene and ethanol, together with side products. It has long been known, for example from EP 0 068 785 A1, that the presence of side products in the low-boiling isobutylene fraction is problematic for subsequent reactions of the isobutylene, in particular in oxidation to methacrylic acid. The isobutylene fraction must therefore generally be purified by removing the side products, as well as methanol or ethanol, before it can be subjected to oxidation to methacrylic acid.

So-called oxyesterification processes are also known, for example from U.S. Pat. No. 4,060,545, U.S. Pat. No. 4,014,925, U.S. Pat. No. 3,925,463, U.S. Pat. No. 3,758,551, U.S. Pat. No. 5,670,702 where oxidation of a propylene or isobutylene and esterification of the oxidised product to an acrylate or a methacrylate takes place in the same reactor. These documents do not address the problem of purification of isobutylene before its oxidation.

An object of the present invention was thus to at least partially overcome some of the problems associated with the prior art. It was particularly desired to avoid the use of highly toxic chemicals in the production of methyl methacrylate.

A further object was to provide a more economical and simpler process for producing methyl methacrylate from a $C_4$ feedstock such as isobutylene and/or TBA.

A particular object of the invention was to reduce the purification effort required for isobutylene before its oxidation.

A contribution to the solution of at least one of the above problems is made by the subject matter of the category-forming claims. The sub-claims dependent on the category-forming claims describe preferred embodiments according to the invention.

Contrary to the expectation that additional compounds such as MTBE, dimethyl ether, formaldehyde and methanol present in the isobutylene feed have a detrimental effect on the oxidation reaction, it has now been surprisingly found that the presence of at least one of the above-mentioned side products, or methanol, during the oxidation of isobutylene and/or TBA to methacrolein and/or methacrylic acid can actually lead to formation of methyl methacrylate during the oxidation.

A contribution to the solution of the above objects is made by a process according to the present invention for preparation of methacrylic acid, comprising the steps:

a) providing a feed composition comprising at least one main compound selected from isobutylene, tert-butyl alcohol and methacrolein and at least one co-compound selected from the group consisting of methanol, dimethyl ether, ethanol, methyl tert-butyl ether, ethyl tert-butyl ether and formaldehyde;

b) subjecting the feed composition obtained in step a) with at least a first part of said at least one co-compound to a catalytic reaction zone and obtaining an oxidation phase comprising methyl methacrylate and at least one of methacrolein and methacrylic acid.

A contribution to the solution of the above objects is also made by a process according to the present invention for preparation of methyl methacrylate, comprising the steps:

a) providing a feed composition comprising at least one main compound selected from isobutylene, tert-butyl alcohol and methacrolein and at least one co-compound selected from the group consisting of methanol, dimethyl ether, ethanol, methyl tert-butyl ether, ethyl tert-butyl ether and formaldehyde;

b) subjecting the feed composition obtained in step a) with at least a first part of said at least one co-compound to a catalytic reaction zone and obtaining an oxidation phase comprising methyl methacrylate and at least one of methacrolein and methacrylic acid;

c) esterification of at least a part of the oxidation phase obtained in step b).

In a preferred aspect of the present invention, the feed composition preferably comprises isobutylene and/or TBA, as well as methanol and/or dimethyl ether and/or formaldehyde as co-compound, more preferably isobutylene and/or TBA with methanol or isobutylene and/or TBA with dimethyl ether, preferably isobutylene with dimethyl ether. Any or all of these can be optionally purified by suitable techniques known to the skilled person, such as distillation, extraction, chromatography, washing, crystallisation or the like, before being provided to the feed composition.

If TBA is to be comprised as feed compound in the feed composition, this may be obtained commercially, prepared from isobutylene and water, for example from a source of isobutylene as described above, or alternatively obtained from propene oxide production via hydroperoxydation as described in U.S. Pat. No. 5,424,458, U.S. Pat. No. 5,436,376, U.S. Pat. No. 5,274,138, Ullmans encyclopedia, $5^{th}$ Edition, Vol. A4, p. 492 and references cited therein.

In a preferred embodiment of the process according to the invention, the feed composition provided in step a) is obtained by splitting of methyl tert-butyl ether or of ethyl tert-butyl ether (ETBE). MTBE is widely used as feedstock for isobutylene and splitting of MTBE is well known in the art. Splitting of ETBE can be achieved as for MTBE. Thus, splitting of MTBE or ETBE can occur by any suitable means which are known to the skilled person. Suitable catalysts and reaction conditions are described, for example, in EP 1 149 814 A1, WO 04/018393 A1, WO 04/052809 A1; Ullmann's Encyclopedia of Industrial Chemistry, $5^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, $5^{th}$ Edition, Vol. A16, p. 543-550; A. Chauvel, G. Lefebvre, "Petrochemical Processes, Technical and Economic Characteristics", Vol. 1, Editions Technip, Paris, 1989, p. 213 et seq.; U.S. Pat. No. 5,336, 841, U.S. Pat. No. 4,570,026, and references cited therein. The disclosures of these references are hereby incorporated by reference and form part of the disclosure of the present invention.

The two main products of MTBE splitting are isobutylene and methanol. The two main products of ETBE splitting are isobutylene and ethanol. Further components which are often also present in the splitting phase resulting from the MTBE splitting are, among others, dimethyl ether, tert-butyl alcohol, methyl sec-butyl ether (MSBE) and unreacted MTBE. Further components present in the splitting phase resulting from the ETBE splitting can be diethyl ether, tert-butyl alcohol, ethyl sec-butyl ether (ESBE) and unreacted ETBE.

In one aspect of the process according to the invention, the splitting phase may be provided directly as feed composition without purification. In a preferred aspect of the process according to the invention, the splitting phase obtained from an MTBE or ETBE splitting reaction is subjected to at least one of at least partial separation and/or purification before being used as feed composition. Suitable purification and separation processes are described, for example, in EP 1 149 814 A1, WO 04/018393 A1 and WO 04/052809A1. In a particularly preferred aspect of the process according to the invention, at least a part of at least one co-compound is separated from the optionally purified splitting phase to form a co-compound phase and a depleted splitting phase which is depleted in the separated at least one co-compound. The depleted splitting phase which comprises isobutylene as main component, can then be optionally purified and provided as feed composition. Suitable purification methods are known to the person skilled in the art and preferably comprise at least one of distillation, extraction, adsorption, absorption, chromatography or washing, preferably at least one of distillation and extraction, preferably at least one distillation and at least one extraction. It is preferred that in this process step at least one of methanol, MTBE, ethanol and ETBE is at least partially separated from the isobutylene phase. Separated MTBE and ETBE can be optionally purified and at least partially recycled to the splitting reaction.

The separated co-compound phase, which preferably comprises methanol as main component in the case of MTBE splitting and ethanol as main component in the case of ETBE splitting, preferably corresponds to the at least one further part of the at least one co-compound which is subjected to esterification in step c).

It is preferred that at least a first part of the at least one co-compound can be subjected to the catalytic reaction zone in step b). This first part of the at least one co-compound preferably at least partially reacts in step b) with at least a part of at least one oxidation product of isobutylene and/or TBA, preferably with methacrolein or methacrylic acid, to form methyl methacrylate. The oxidation phase exiting the catalytic reaction zone thus preferably comprises methacrylic acid as main product, as well as at least a part of methyl methacrylate.

It is preferred in the process according to the invention that in step b) the feed composition has a content of not less than 5 ppm, preferably not less than 6 ppm, preferably not less than 7 ppm, preferably not less than 8 ppm, more preferably not less than 9 ppm and yet more preferably not less than 10 ppm of the at least one co-compound as at least a first part of the at least one co-compound. An upper limit for the content of co-compound in the feed composition is about 50 wt. %, based on the feed composition.

It is particularly preferred in the process according to the invention that in step b) the feed composition comprises at least a first part of the at least one co-compound in a range from 0.0005 to 10 wt. %, preferably from 0.0008 to 8 wt. %, more preferably from 0.001 to 7 wt. %, yet more preferably from 0.001 to 6 wt. %, more preferably from 0.001 to 5 wt. %, more preferably from 0.005 to 4 wt. %, more preferably from 0.01 to 3 wt. %, even more preferably from 0.1 to 2.7 wt. %, more preferably from 0.5 to 2.5 wt. %.

To the feed composition is preferably added a source of oxygen, which source is not limited and can be any suitable source of oxygen ($O_2$) such as peroxide, molecular oxygen or oxygen-enriched or oxygen-comprising gas, whereby air is preferred as oxygen source for economic reasons. An $O_2$ source is understood here to be any compound or composition that comprises or liberates $O_2$. The amount of molecular oxygen provided as $O_2$ or as $O_2$ source is preferably from about 0.5 to about 20 moles, preferably from about 1 to about 10 moles $O_2$ per mole of isobutylene and/or TBA, more preferably from about 1 to about 5 moles $O_2$ per mole of isobutylene and/or TBA, more preferably from about 1 to about 3 moles $O_2$ per mole of isobutylene and/or TBA, more preferably from about 1 to about 2 moles $O_2$ per mole of isobutylene and/or TBA. Water and/or water vapour can also be added to the feed composition. If water and/or water vapour is added to the feed composition it is preferred that from about 1 to about 20 moles, preferably from about 1 to about 15 moles, preferably from about 1 to about 10 moles, more preferably from about 1 to about 8 moles of water and/or water vapour is added to the feed composition, per mole of isobutylene and/or TBA. It may not be preferred to comprise water and/or water vapour in the feed composition at the start of step b) to the extent that TBA is comprised therein. It is further preferred that at least one diluent is added to the feed composition, which diluent can comprise inorganic or organic solvent or a gas, preferably at least one diluent gas which is inert under the reaction conditions, preferably selected from nitrogen, argon, carbon dioxide, whereby nitrogen gas and/or carbon dioxide, preferably carbon dioxide recycled from a combustion unit, preferably a catalytic or thermal combustion unit, is preferred as diluent gas.

According to the process according to the invention, in step b) the feed composition is preferably subjected to oxidation to obtain at least one oxidation product of isobutylene and/or TBA. The oxidation is preferably a catalytic oxidation, preferably a gas phase catalytic oxidation. Suitable reaction conditions for gas phase catalytic oxidation are, for example, temperatures of from about 250° C. to about 450° C., preferably from about 250° C. to about 390° C. and pressures of from about 1 atm. to about 5 atm. The space velocity can vary from about 100 to about 6000 $hr^{-1}$ (NTP) and preferably from about 500 to about 3000 $hr^{-1}$. Oxidation, for example gas phase catalytic oxidation, of $C_4$ feeds such as isobutylene to methacrolein and/or methacrylic acid, as well as catalysts therefor, are well known in the literature, for example from U.S. Pat. No. 5,248,819, U.S. Pat. No. 5,231,226, U.S. Pat. No. 5,276,178, U.S. Pat. No. 6,596,901 B1, U.S. Pat. No. 4,652,673, U.S. Pat. No. 6,498,270, U.S. Pat. No. 5,198,579, U.S. Pat. No. 5,583,084.

The at least one oxidation product of isobutylene and/or TBA can be any oxygen-comprising product based on isobutylene and/or TBA, preferably at least one $C_4$ oxidation product such as a $C_4$ alcohol, a $C_4$ aldehyde or a $C_4$ acid, whereby at least one of methacrolein and/or methacrylic acid are preferred oxidation products.

In a preferred embodiment of the process according to the invention, the oxidation in step b) takes place in a single oxidation stage. If the process according to the invention comprises a single oxidation stage in step b), it is preferred that the resulting oxidation phase comprises methacrylic acid as main component.

In another preferred embodiment of the process according to the invention, the oxidation in step b) takes place in at least two separate oxidation stages, preferably in two separate oxidation stages. These at least two oxidation stages can be oxidation stages within a same area of the catalytic reaction zone, for example if the catalytic reaction zone is in the form of one or more reactors, a first oxidation stage can be in a first oxidation area in a reactor and a further oxidation stage can be in a further oxidation area downstream of the first oxidation area in the same reactor, or a first oxidation stage can be in a first reactor and a further oxidation stage can be in a further reactor. It is preferred that the first oxidation stage and the further oxidation stage are at different temperatures, and preferably that the first oxidation stage and the further oxidation stage are separated by an intermediate area at a different temperature to that of either of the first and further oxidation stages.

In the process according to the invention comprising two or more oxidation stages, the at least one co-compound can be provided in the feed composition in the first oxidation stage and/or in the feed composition in a subsequent oxidation stage. In the case of a two-stage oxidation, for example, the at least one co-compound can be provided in the feed composition in the first and/or the second oxidation stage. In a preferred embodiment of the process according to the invention the at least one co-compound is provided in the feed composition in the second oxidation stage of a two-stage oxidation.

In an aspect of the process according to the invention comprising a two-stage oxidation, it is preferred that in a first oxidation stage the amount of $O_2$ provided is preferably from about 0.5 to about 10 moles, preferably from about 1 to about 5 moles, more preferably from about 1 to about 3 moles, preferably from about 1 to about 2 moles $O_2$ per mole of isobutylene and/or TBA, and a preferred amount of water and/or water vapour is in the range from 0 to about 20 moles, preferably from 0 to about 10 moles, more preferably from 0 to about 5 moles $H_2O$ per mole of isobutylene and/or TBA, whereby a molar ratio $O_2$:isobutylene and/or TBA:water and/or water vapour of about 2:1:0 is preferred if mainly TBA is provided as $C_4$ feedstock in the feed composition and about 2:1:1 if mainly isobutylene is provided as $C_4$ feedstock in the feed composition. In a second oxidation stage the amount of $O_2$ provided is preferably from about 0.5 to about 10 moles, preferably from about 1 to about 5 moles, more preferably from about 1 to about 3 moles $O_2$ per mole of isobutylene and/or TBA, and a preferred amount of water and/or water vapour is in the range from about 1 to about 20 moles, preferably from about 1 to about 10 moles, more preferably from about 2 to about 8 moles $H_2O$ per mole of isobutylene and/or TBA, whereby a preferred molar ratio $O_2$:isobutylene and/or TBA:water and/or water vapour in a second oxidation stage is in the range of about 2:1:2-6, preferably in the range of about 2:1:3-5, based on the number of moles of isobutylene and/or TBA provided in the feed composition in the first oxidation stage. It is further preferred that at least one diluent is added to the isobutylene phase, which diluent can comprise inorganic or organic solvent or a gas, preferably at least one diluent gas which is inert under the reaction conditions, preferably selected from nitrogen, argon and carbon dioxide, whereby nitrogen gas and/or carbon dioxide, preferably carbon dioxide recycled from a catalytic or thermal combustion unit, preferably from a catalytic combustion unit, is preferred as diluent gas.

If the process according to the invention takes place in at least two separate oxidation stages, it is preferred that the main product of a first oxidation stage is methacrolein and the main product of a further oxidation stage is methacrylic acid. The presence of the at least one co-compound results in a yield of methacrylic acid which is reduced compared to the expected yield of methacrylic acid if the same reaction is carried out on isobutylene in the absence of the at least one co-compound. This reduction is, however, compensated by the unexpected formation of methyl methacrylate already during the oxidation.

The amount of methyl methacrylate present in the oxidation phase is dependent on the amount of co-compound present in the feed composition and on the conversion thereof to methyl methacrylate under the oxidation conditions. It has been found, for example, that when the at least one co-compound is methanol, less than half of the methanol is oxidised to formaldehyde, while up to about 50% of the methanol reacts to methyl methacrylate. An amount of about 2 wt. % methanol, based on the hydrocarbons in the feed composition, in the feed composition thus results in an oxidation phase comprising about 1 wt. % methyl methacrylate, based on the hydrocarbons in the oxidation phase. A similar conversion is also obtained if dimethyl ether is present as co-compound.

While some methyl methacrylate is formed in the first oxidation stage, methyl methacrylate appears to be formed mainly in a further oxidation stage, preferably in a second oxidation stage. In the process according to the invention, the oxidation phase preferably comprises at least 0.0005 wt. %, preferably at least 0.0008 wt. %, more preferably at least 0.001 wt. %, more preferably at least 0.005 wt. %, yet more preferably at least 0.01 wt. %, more preferably at least 0.05 wt. %, preferably at least 0.1 wt. %, preferably at least 0.3 wt. %, more preferably at least 0.5 wt. %, more preferably at least 0.8 wt. %, yet more preferably at least 1 wt. %, even more preferably 1.5 wt. %, more preferably at least 1.2 wt. %, more preferably at least 1.5 wt. %, even more preferably at least 1.8 wt. %, more preferably at least 2 wt. % methyl methacrylate, based on the hydrocarbons in the oxidation phase.

The oxidation phase is preferably subjected to at least one of quenching and/or purification to isolate the methacrylic acid, preferably the methacrylic acid and the methyl methacrylate, and to remove unreacted feed composition compounds such as methacrolein and/or undesired side products arising from the reaction or reactions in the catalytic reaction zone. The quenching can be carried out by any suitable quenching process known to the skilled person, as described for example in Offenlegungsschrift DE 21 36 396, EP 297 445 A2, EP 297 788 A2, JP 01193240, JP 01242547, JP 01006233, US 2001/0007043 A1, U.S. Pat. No. 6,596,901 B1, U.S. Pat. No. 4,956,493, U.S. Pat. No. 4,618,709 B1, U.S. Pat. No. 5,248,819, whose disclosure concerning quenching of acrylic and methacrylic acids is hereby incorporated and forms part of the present disclosure. Preferred quenching agents are water and organic solvents such as, for example, aromatic or aliphatic hydrocarbons, or mixtures of at least two thereof, whereby preferred organic solvents have relatively low vapour pressure under the quenching conditions, such as heptane, toluene or xylene. The purification can be carried out by any suitable purification means known to the skilled person, such as by distillation, crystallisation, extraction, absorption or precipitation, preferably by crystallisation. Such purification techniques are well known in the art, for example in JP 01193240, JP 01242547, JP 01006233, DE 100 39 025 A1, US 2003/0175159, DE 100 36 881 A1, EP 297 445 A2, U.S. Pat. No. 6,596,901 B1, U.S. Pat. No. 6,646,161 B1, U.S. Pat. No. 5,248,819, U.S. Pat. No. 4,618,709 B1, and references cited therein. Reference is hereby explicitly made to these disclosures concerning purification and they form part of the disclosure of the present invention.

It is preferred that in a quenching step and/or in a purification step methacrolein is separated. The separated methacrolein can be recycled to the catalytic reaction zone, whereby if the catalytic reaction zone comprises more than one oxidation stage the separated methacrolein is preferably recycled to a further oxidation stage, preferably to the second oxidation stage of a catalytic reaction zone comprising two oxidation stages. In this way, the separated methacrolein can be further subjected to oxidation, thereby leading to increased efficiency of the overall process and increased yields of methacrylic acid and methyl methacrylate.

Methacrylic acid produced in steps a) and b) above can be at least partially collected, or it can be conducted to further reactions or processes. At least one polymerisation inhibitor is preferably added to the methacrylic acid. Manipulation of methacrylic acid in at least one process step, in particular in any process step taking place at increased temperature, preferably takes place in the presence of a polymerisation inhibitor.

In the process according to the invention for preparation of methyl methacrylate, the generally optionally but in some cases necessarily quenched and/or purified oxidation phase comprising at least one oxidation product is subjected to esterification in step c), optionally in the presence of a polymerisation inhibitor to prevent polymerisation of methacrylic acid and/or methyl methacrylate. The means of carrying out the esterification in step c) is not particularly limited. The esterification can be carried out, for example, as described in U.S. Pat. No. 6,469,202, JP 1249743, EP 1 254 887 A1, U.S. Pat. No. 4,748,268, U.S. Pat. No. 4,474,981, U.S. Pat. No. 4,956,493 or U.S. Pat. No. 4,464,229 whose disclosures concerning esterification of acrylic and methacrylic acids are hereby incorporated and form part of the present disclosure. An oxyesterification is also possible, for example as described in the literature cited above.

According to a preferred aspect of the invention, at least a further part of said at least one co-compound, preferably at least 80 wt. %, more preferably at least 90 wt. % and most preferably in the range from 95 to 99 wt. %, each based on said at least one co-component, is subjected to esterification in step c). According to one embodiment of the present invention it is possible that this at least one further part of the at least one co-compound is separated from the at least one part of the at least one co-compound before providing the at least one co-compound to the feed composition. According to a further embodiment of the present invention it possible that the at least one further part of the at least one co-compound is separated from the feed composition before subjecting the feed composition to the catalytic reaction zone. The separated at least one further part of the at least one co-compound can then be provided again, for example by combining it with the optionally quenched and/or purified oxidation phase before and/or during the esterification in step c), and subjected to esterification together with the optionally quenched and/or purified oxidation phase. This aspect is particularly preferred if at least methanol is present as co-compound. The at least one further part of the at least one co-compound can be subjected to purification before it is subjected to the esterification in step c). Suitable purification techniques are known to the skilled person, for example those mentioned above in connection with the at least one co-compound in the feed composition.

In the process according to the invention for preparation of methyl methacrylate, the esterification phase produced is step c) is optionally subjected to a purification, whereby preferably methyl methacrylate is separated from other esterification phase components such as unreacted methanol and/or methacrylic acid and other impurities. Suitable purification methods are known to the person skilled in the art and preferably comprise at least one of distillation, crystallisation, extraction, chromatography or washing more preferably at least one distillation device. Separated methanol and/or methacrylic acid can be recycled to other reaction steps, or to the esterification step, optionally after purification, or can be collected.

According to a further embodiment of the invention, it is possible that any or all of steps a) to c) occur at least partially in liquid phase and/or in the gas phase. Thus it is possible that all steps occur at least partially in liquid phase, that all steps occur at least partially in the gas phase, or that at least one step occurs at least partially in the liquid phase and the remaining step or steps occur at least partially in the gas phase. In preferred aspects of the invention, steps a) and b) occur at least partially in the gas phase and step c) at least partially in the liquid phase, or steps a), b) and c) occur at least partially in the liquid phase. It is particularly preferred according to the process according to the invention that at least step b) occurs at least partially in the gas phase. If step b) comprises at least two oxidation stages, it is possible that at least one oxidation stage occurs at least partially in liquid phase and at least one oxidation stage occurs at least partially in the gas phase.

If step b) occurs at least partially in the gas phase, it is preferred that a quenching step as described above is carried out prior to purification of the oxidation phase.

In an embodiment of the process according to the invention wherein in step b) the oxidation takes place in two separate oxidation stages, it is possible that one or both of the oxidation stages are gas phase or liquid phase oxidation stages. It is also possible that one oxidation stage is a gas phase oxidation stage and the other oxidation stage is a liquid phase oxidation stage. In a preferred aspect of the process according to the invention, the first and second oxidation stages are gas phase oxidation stages. In another preferred aspect of the process according to the invention, the first oxidation stage is a gas phase oxidation stage and the second oxidation stage is a liquid phase oxidation stage. It is preferred that the esterification of step c) is a liquid phase esterification. If the second oxidation stage is a liquid phase oxidation stage it is also possible that this second oxidation stage is combined with step c) into a combined liquid phase oxidation-esterification stage.

In an embodiment of the process according to the invention where the oxidation takes place in at least two separate oxidation stages, it is possible that a quenching step takes place between at least two of the at least two separate oxidation stages. This quenching step is preferably a quenching step enabling isolation of methacrolein. This embodiment can be particularly preferred if a second or further oxidation stage is a liquid phase oxidation stage, or if a second or further oxidation stage is combined with step c) into a combined liquid phase oxidation-esterification stage. Quenching of this type can be carried out by any suitable method known to the skilled person. Suitable methods are described, for example, in DE 34 41 207 A1 and in JP 60087241.

If step c) occurs in the gas phase, dimethyl ether is preferred as co-compound. If step c) occurs in the liquid phase, methanol is preferred as co-compound.

It is preferred in the process according to the invention that the at least one further part of said at least one co-compound, which is subjected to esterification in step c) as described above, is at least 90 wt. %, more preferably at least 92 wt. %, more preferably at least 93, 94, 95 or 96 wt. %, even more preferably at least 97 wt. %, yet more preferably at least 97.5 wt. %, more preferably at least 98 wt. % of the at least one co-compound. Thus, for example, if the feed composition is obtained from splitting of MTBE, it is preferred that at least 90 wt. %, more preferably at least 92 wt. %, more preferably at least 93, 94, 95 or 96 wt. %, even more preferably at least 97 wt. %, yet more preferably at least 97.5 wt. %, more preferably at least 98 wt. % of the methanol produced in the splitting is separated from the splitting phase, optionally purified, and subjected to esterification in step c).

A contribution to the solution of the objects underlying the present invention is also provided by an apparatus for production of methacrylic acid, comprising:
i) a supply for a feed composition comprising at least one main compound selected from isobutylene, tert-butyl alcohol and methacrolein and at least one co-compound selected from the group consisting of methanol, dimethyl ether, ethanol, methyl tert-butyl ether, ethyl tert-butyl ether and formaldehyde; in fluid communication with
ii) a catalytic reaction zone for at least partial conversion of the feed composition into methyl methacrylate; in fluid communication with
iii) optionally, at least one first purification unit;
v) optionally, a conduit unit; connected in fluid communication at least to the supply.

A contribution to the solution of the objects underlying the present invention is also provided by an apparatus for production of methyl methacrylate, comprising:
i) a supply for a feed composition comprising at least one main compound selected from isobutylene, tert-butyl alcohol and methacrolein and at least one co-compound selected from the group consisting of methanol, dimethyl ether, ethanol, methyl tert-butyl ether, ethyl tert-butyl ether and formaldehyde; in fluid communication with
ii) a catalytic reaction zone for at least partial conversion of the feed composition into methyl methacrylate; in fluid communication with
iii) optionally, at least one first purification unit; in fluid communication with
iv) an esterification unit;
v) optionally, a conduit unit; connected in fluid communication at least to the supply and to the esterification unit.

The supply can be any means suitable for supplying a feed composition to the catalytic reaction zone, for example a reservoir, a pipe, a line, a tube, or the like. The supply should preferably be resistant to elevated and/or decreased temperature and/or pressure, preferably resistant at least to temperatures and pressures as described above for a preferred oxidation reaction. A good temperature and/or pressure resistance is particularly preferred if one or more of the reactions which should take place in the apparatus is a gas phase reaction. The supply is furthermore preferably not reactive with any of the components of the feed composition, nor with any further component such as oxygen or an oxygen equivalent, water or water vapour, diluent, which might be added to the feed composition, as mentioned above in connection with the process according to the invention. Any supply which is intended to supply a gaseous phase or composition is preferably maintained at a temperature above the dewpoint temperature of the gas to be supplied. This can be achieved, for example, by heating or by thermally insulating the supply.

In a preferred embodiment of the apparatus according to the present invention, the supply is preferably in fluid communication with a methyl tert-butyl ether or ethyl tert-butyl ether splitting unit. The term "in fluid communication" is understood here as meaning that the supply is connected with the splitting unit such that a fluid, which can be at least one of a liquid, a gas, a vapour, a supercritical fluid or any other fluid, can be conveyed and or transported by any means, preferably flow, from the supply to the splitting unit or from the splitting unit to the supply. Splitting units for MTBE and ETBE are well known in the art and form part of the general knowledge of the skilled person, as described, for example, in Ullmann's Encyclopedia of Industrial Chemistry, 5$^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, 5$^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein.

In the apparatus according to the invention, the catalytic reaction zone preferably comprises at least one oxidation unit. The at least one oxidation unit is preferably at least one oxidation unit suitable for carrying out oxidation of isobutylene and/or TBA to at least one of methacrolein and methacrylic acid, preferably comprising at least one oxidation catalyst. The at least one oxidation unit can be, for example, a multitube reactor such as a tube and shell reactor, a plate reactor or a fluidised bed reactor, whereby a multitube reactor is preferred, preferably a multitube reactor packed with oxidation catalyst. Such reactors are commercially available, for example from MAN DWE GmbH, Deggendorfer Werft, Germany, or from Ishikawajima-Harima Heavy Industries (IHI Corporation from 1 Jul. 2007), Japan, and form part of the general knowledge of the person skilled in the art.

In a preferred embodiment of the apparatus according to the invention, the catalytic reaction zone comprises one oxidation area, preferably one oxidation unit, preferably one oxidation reactor, whereby it is preferred that this oxidation area comprises at least one catalyst, preferably a catalyst capable of oxidation of at least one of isobutylene and TBA to at least one of methacrolein and methacrylic acid, preferably to methacrylic acid.

In another preferred embodiment of the apparatus according to the invention, the catalytic reaction zone, preferably the at least one oxidation unit, comprises at least a first oxidation area and a further oxidation area, preferably a first oxidation area and a second oxidation area. The first oxidation area and the further oxidation area, preferably the first oxidation area and the second oxidation area, can be different oxidation areas in a single reactor, or they can each be in a separate respective reactor, with all reactors being in fluid communication with each other. In an embodiment where the catalytic reaction zone is in the form of one reactor, a first oxidation stage is preferably in a first oxidation area in a reactor and a further oxidation stage is then in a further oxidation area downstream of the first oxidation area in the same reactor. In a preferred aspect, the reactor is a multitube reactor as described above. In this case it is preferred that at least one oxidation catalyst, preferably at least two oxidation catalysts, are provided, preferably in a layered-type fashion, preferably such that a first oxidation stage occurs at least one upstream catalyst layer and a further oxidation stage at least one further catalyst layer downstream thereof. Catalyst layers in a same tube can be directly adjacent to each other. It is also possible that at least one catalyst layer is separated from at least one other catalyst layer by at least one intermediate area, for example at least one mixing area or at least one transition area, e.g. at least one transition area between an area with a certain number of tubes and an area with a different number of tubes, or by means of layers of, for example, packing materials or suspending agents which are inert under the reaction conditions. If, in a process where the first oxidation and a further oxidation occur in the gas phase, the first oxidation area and the further oxidation area are in separate reactors, it is preferred that all reactors are multitube reactors. On the other hand, if at least one reactor is a liquid phase reactor, for example a liquid phase oxyesterification reactor, this reactor is preferably not a multitube reactor.

It is additionally preferred that the first oxidation area and the further oxidation area or areas are at different temperatures. It is further preferred that the first and further oxidation areas, in particular if they are at different temperatures with respect to each other, are separated by an intermediate area which is at a different temperature to that of either of the first and further oxidation stages.

If the apparatus according to the invention comprises a first oxidation reactor and at least one further oxidation reactor as described above, it is possible that a quenching unit is provided after the first oxidation reactor and before at least one further oxidation reactor, preferably between the first and second oxidation reactors. This quenching unit preferably serves to isolate methacrolein. A quenching unit between the first oxidation reactor and at least one further oxidation reactor is preferred if the first oxidation reactor is a gas phase reactor and the at least one further reactor is a liquid phase reactor.

Quenching units suitable for use in the apparatus are preferably those as described, for example, in the references cited above in connection with a quenching process step.

It is preferred in the apparatus according to the invention that, if the apparatus comprises a first oxidation area and a further oxidation area, the first oxidation area comprises a first oxidation catalyst and the further oxidation area comprises a further oxidation catalyst, whereby the further oxidation area is preferably a second oxidation area and the further oxidation catalyst is preferably a second oxidation catalyst. The first oxidation catalyst is preferably a catalyst for oxidation of isobutylene to methacrolein, and the further oxidation catalyst, preferably the second oxidation catalyst, is preferably a catalyst for oxidation of methacrolein to methacrylic acid. The first and further catalysts are not particularly limited and are preferably solid catalysts suitable for the oxidation, preferably mixed metal oxide catalysts. Such catalysts are well known in the art, for example as described in JP 58059934, JP 55045617, EP 0 005 769 A1, EP 1 350 566 A2, EP 0 450 596 A2, EP 0 456 837 A1, WO 2001/098247 A2, EP 0 630 879 A1, US 2002/0198406 A1, EP 911 313, U.S. Pat. No. 5,602,280, EP 145 469, U.S. Pat. No. 5,218,146, U.S. Pat. No. 4,365,087, U.S. Pat. No. 5,077,434, U.S. Pat. No. 5,231,226 or US 2003/0004374 A1, U.S. Pat. No. 6,498,270 B1, U.S. Pat. No. 5,198,579, EP 1 595 600 A1, EP 1 052 016 A2, U.S. Pat. No. 5,583,084, and references cited therein, whose disclosure concerning oxidation catalysts is hereby incorporated by reference and forms a part of the disclosure of the present invention. If a first and a further oxidation catalyst are comprised they are preferably arranged in the at least one oxidation area as described above.

In a preferred aspect of the apparatus of the present invention, at least one supply for at least one $O_2$ source, preferably at least one supply for air, and at least one supply for water and/or steam, are in fluid communication with at least one of the catalytic reaction zone and the supply. It is preferred according to the invention that the at least one supply for at least one $O_2$ source and the at least one supply for water and/or steam provide respectively at least one $O_2$ source and water and/or steam directly to the catalytic reaction zone. If the catalytic reaction zone comprises at least a first and a further oxidation area, the apparatus preferably comprises at least one supply for at least one $O_2$ source and at least one supply for water and/or steam for each oxidation area. The apparatus can further comprise a supply for a diluent such as nitrogen, argon and/or carbon dioxide, preferably nitrogen or carbon dioxide, preferably carbon dioxide-comprising recycle gas from a catalytic combustion unit (CCU) or a thermal combustion unit (TCU), preferably from a catalytic combustion unit.

The apparatus according to the invention optionally comprises at least one first purification unit downstream of the catalytic reaction zone. In the apparatus for production of methyl methacrylate, the at least one first purification unit is upstream of the esterification unit, preferably between and in fluid communication with the catalytic reaction zone and the esterification unit. The at least one second purification unit is preferably suitable for purification of methacrylic acid, preferably for separation of methacrylic acid from water and/or terephthalic acid (TPA), and preferably comprises at least one of a distiller, a crystalliser, an extractor, a wash device and a column. It is particularly preferred that the at least one first purification unit comprises at least one crystalliser. It is possible that the at least one first purification unit comprises more than one purification stage. Unreacted methacrolein can be separated here and, if desired, conducted back to the catalytic reaction zone for further reaction. Suitable purification units are described in the references cited above in connection with a process step for purification of methacrylic acid.

In a preferred embodiment of the apparatus according to the invention, at least one quench unit is comprised between and in fluid communication with the catalytic reaction zone and the purification unit. It is preferred that methacrylic acid present in the oxidation phase leaving the catalytic reaction zone is condensed in the quench unit to form a solution comprising methacrylic acid as main oxidation product. Unreacted methacrolein can also be separated in the quench unit and, if desired, conducted back to the catalytic reaction zone for further reaction. Quench units suitable for use in the apparatus according to the invention are described, for example, in the references cited above in connection with a quenching process step and an intermediate quenching step.

The esterification unit is not particularly limited and can be any unit suitable for esterification to form methyl methacrylate. It is preferably suitable for liquid phase esterification. The esterification unit preferably comprises an esterification catalyst, which can be a heterogeneous or homogeneous catalyst such as a solid state catalyst or a liquid catalyst, and is preferably an acidic ion exchange resin such as those described in U.S. Pat. No. 6,469,292, JP 1249743, EP 1 254 887 A1 or commercially available under the trade name names Amberlyst® (Rohm and Haas Corp.), Dowex®, (Dow Corp.) or Lewertit® (Lanxess AG), or an acid capable of catalysing esterification, such as sulphuric acid, $H_2SO_4$.

The conduit unit is preferably in fluid communication with at least the supply and the esterification unit. If an MTBE or ETBE splitter is comprised in the apparatus, the conduit unit is preferably also connected to the MTBE or ETBE splitter, preferably between the MTBE or ETBE splitter and the supply, as well as between the MTBE or ETBE splitter and the esterification unit.

In a preferred aspect of the apparatus according to the invention, the conduit unit comprises means for separating at least a part of the at least one co-compound. Such means can be, for example, a distiller, a column, an extractor, a tap, a pipe, a valve, a regulator, a phase separator, or any other means known to the skilled person and appearing suitable for separating a liquid from a liquid, a liquid from a gas and/or vapour or a gas and/or vapour from a gas and/or vapour.

The apparatus according to the invention preferably comprises, between a splitting unit and the catalytic reaction zone, or between the conduit unit and the supply or between the MTBE or ETBE splitter and the conduit unit and preferably in fluid communication with at least two thereof, at least one separation and/or purification unit for separation and/or purification of an isobutylene phase from the effluent of the splitting unit. The separation and/or purification unit can be at least one of an extractor, a crystalliser, a column, a distillation device, a rectification device, a membrane, a pervaporation device, an adsorption unit, an absorption unit and a wash device.

The apparatus can further comprise at least one third purification unit between the conduit unit and the esterification unit. The third purification unit or units is preferably at least one purification unit for at least one co-compound, preferably for methanol. Suitable purification units are known to the person skilled in the art and preferably comprise at least one distillation device, crystalliser, extractor, column or wash device, more preferably at least one distillation device. An example of a purification unit for methanol is described in EP 1 254 887 A1.

The apparatus may further comprise at least one fourth purification unit downstream of the esterification unit, for purification of methyl methacrylate. Suitable purification units are known to the person skilled in the art and preferably comprise at least one distillation device, crystalliser, extractor, column or wash device, more preferably at least one distillation device. The at least one fourth purification unit should enable the at least partial purification of methyl methacrylate and at least partial separation of side products, for example impurities arising from the esterification, unreacted methanol and/or methacrylic acid. Unreacted reagents can optionally be recycled into the esterification reaction, optionally after being subjected to purification.

The invention also relates to a process according to the invention for preparation of methacrylic acid, wherein said process is performed in an apparatus according to the invention.

The invention also relates to methacrylic acid obtainable by a process according to the invention.

The invention also relates to a process according to the invention for preparation of methyl methacrylate, wherein said process is performed in an apparatus according to the invention.

The invention also relates to methyl methacrylate obtainable by a process according to the invention.

The invention also relates to a process for preparation of a methacrylate ester with formula $[CH_2=C(CH_3)C(=O)O]_n$—R, comprising process steps α1 preparation of methacrylic acid according to a process according to the present invention; or α2 preparation of methyl methacrylate according to a process according to the present invention; and α3 reaction of the methacrylic acid obtained in step α1 or of the methyl methacrylate obtained in step α2 with an alcohol of formula $R(OH)_m$, whereby n and m represent an integer from 1 to 10, preferably from 1 to 6, more preferably from 1 to 5, more preferably from 1 to 4, more preferably from 1 to 3 and R is selected from the group consisting of linear or branched, saturated or unsaturated, aliphatic or aromatic, ring or straight chain hydrocarbons and linear or branched, saturated or unsaturated, aliphatic or aromatic, ring or straight chain hetero-atom-comprising hydrocarbons, for example alkyls, hydroxyalkyls, aminoalkyls, other nitrogen- and/or oxygen-comprising residues, glycols, diols, triols, bisphenols, fatty acid residues, whereby R preferably represents butyl, in particular n-butyl, isobutyl, hydroxyethyl, preferably 2-hydroxyethyl, and hydroxypropyl, preferably 2-hydroxypropyl or 3-hydroxypropyl, ethyl, 2-ethylhexyl, isodecyl, cyclohexyl, isobornyl, benzyl, 3,3,5-trimethyl cyclohexyl, stearyl, dimethylaminoethyl, dimethylaminopropyl, 2-tert-butyl aminoethyl, ethyl triglycol, tetrahydrofurfuryl, butyl diglycol, methoxypolyethylene glycol-350, methoxypolyethylene glycol 500, methoxypolyethylene glycol 750, methoxypolyethylene glycol 1000, methoxypolyethylene glycol 2000, methoxypolyethylene glycol 5000, allyl, ethylene glycol, diethylene glycol, triethylene glycol, polyethylene glycol 200, polyethylene glycol 400, 1,3-butanediol, 1,4-butanediol, 1,6-hexanediol, glycerol, diurethane, ethoxylated bisphenol A, ethoxylated bisphenol A with 10 ethylene oxide units; trimethylolpropane, an ethoxylated $C_{16}$-$C_{18}$ fatty alcohol such as, for example, with 25 ethylene oxide units, 2-trimethylammonium ethyl.

The methacrylate ester derivatives can be prepared in step α3 from methyl methacrylate by methods known to the skilled person, for example by transesterification. Alternatively, these derivatives may be prepared in step α3 by esterification of methacrylic acid according to the invention with the respective alcohol. In a further possible preparation of the hydroxyester derivatives, methacrylic acid according to the invention is reacted in a ring-opening reaction with a corresponding oxygen-comprising ring, for example an epoxide, in particular ethylene oxide or propylene oxide.

The invention also relates to a methacrylate ester with formula $[CH_2=C(CH_3)C(=O)O]_n$—R, wherein n and R are as defined above. Preferred methacrylate esters are alkyl methacrylates, in particular butyl methacrylates, in particular n-butyl methacrylate, isobutyl methacrylate, hydroxyester methacrylate derivatives, for example hydroxyethyl methacrylate, preferably 2-hydroxyethyl methacrylate, and hydroxypropyl methacrylate, preferably 2-hydroxypropyl methacrylate or 3-hydroxypropyl methacrylate, and special methacrylate esters ethyl methacrylate, 2-ethylhexyl methacrylate, isodecyl methacrylate, cyclohexyl methacrylate, isobornyl methacrylate, benzyl methacrylate, 3,3,5-trimethyl cyclohexyl methacrylate, stearyl methacrylate, dimethylaminoethyl methacrylate, dimethylaminopropyl methacrylate, 2-tert-butyl amino ethyl methacrylate, ethyl triglycol methacrylate, tetrahydrofurfuryl methacrylate, butyl diglycol methacrylate, methoxypolyethylene glycol-350 methacrylate, methoxypolyethylene glycol 500 methacrylate, methoxypolyethylene glycol 750 methacrylate, methoxypolyethylene glycol 1000 methacrylate, methoxypolyethylene glycol 2000 methacrylate, methoxypolyethylene glycol 5000 methacrylate, allyl methacrylate, a methacrylic ester of an ethoxylated (optionally, for example, with 25 mol EO) $C_{16}$-$C_{18}$ fatty alcohol, 2-trimethylammonium ethyl methacrylate chloride; ethylene glycol dimethacrylate, diethylene glycol dimethacrylate, triethylene glycol dimethacrylate, polyethylene glycol 200 dimethacrylate, polyethylene glycol 400 dimethacrylate, 1,3-butanediol dimethacrylate, 1,4-butanediol dimethacrylate, 1,6-hexanediol dimethacrylate, glycerol dimethacrylate, diurethane dimethacrylate, ethoxylated bisphenol A dimethacrylate, ethoxylated (optionally, for example, with 10 EO) bisphenol A dimethacrylate; trimethylolpropane trimethacrylate.

The invention further relates to a process for producing a polymer comprising at least one monomer unit selected from methacrylic acid, methyl methacrylate and a methacrylic ester with formula $[CH_2=C(CH_3)C(=O)O]_n$—R, wherein n and R are as defined above, comprising the steps:

A1. preparation of at least one of methacrylic acid, methyl methacrylate and at least one methacrylate ester according to a process according to the invention, A2. polymerisation of
  A2a. at least one of the methacrylic acid, the methyl methacrylate and the at least one methacrylate ester obtained in step A1, and
  A2b. optionally at least one co-monomer which is co-polymerisable with at least one of methacrylic acid, methyl methacrylate and at least one methacrylate ester.

The polymerisation is not particularly limited and can be carried out by any method known to the skilled person and appearing suitable, for example as described in U.S. Pat. No. 5,292,797, U.S. Pat. No. 4,562,234, U.S. Pat. No. 5,773,505, U.S. Pat. No. 5,612,417, U.S. Pat. No. 4,952,455, U.S. Pat. No. 4,948,668, U.S. Pat. No. 4,239,671. Preferred polymerisation methods are radical polymerisation, initiated by initiators which decompose into radicals under the polymerisation conditions, whereby the polymerisation is preferably a solution or an emulsion polymerisation, preferably an aqueous solution polymerisation.

Examples of co-monomers which can be co-polymerised with methyl methacrylate are acrylamides and methacrylamides, acrylic acid esters and other methacrylic acid esters, such as methyl acrylate, ethyl acrylate, propyl acrylate or butyl acrylate, ethyl methacrylate, propyl methacrylate or butyl methacrylate, as well as acetates such as vinyl acetate, styrene, butadiene and acrylonitrile. The at least one co-monomer is most preferably at least one co-monomer selected from the group consisting of: styrene, butadiene, acrylonitrile, butyl acrylate, vinyl acetate, methyl acrylate.

The polymerisation can also take place in the presence of one or more crosslinkers. Preferred cross-linkers according to the invention are compounds which have at least two ethylenically unsaturated groups in one molecule, compounds which have at least two functional groups which can react with functional groups of the monomers in a condensation reaction, in an addition reaction or a ring-opening reaction, compounds which have at least one ethylenically unsaturated group and at least one functional group which can react with functional groups of the monomers in a condensation reaction, an addition reaction or a ring-opening reaction, or polyvalent metal cations.

The invention also relates to a polymer obtainable according to a process according to the invention or comprising at least one monomer unit selected from a methacrylic acid monomer according to the invention or obtainable by a process according to the invention and a methyl methacrylate monomer according to the invention or obtainable by a process according to the invention and a methacrylate ester according to the invention or obtainable by a process according to the invention, as well as optionally other components such as a co-monomer and optionally a crosslinker.

The invention also relates to a process for producing a composition comprising at least a first component selected from at least one of methacrylic acid according to the invention, methyl methacrylate according to the invention, a methacrylate ester according to the invention, and a polymer comprising at least one monomer unit selected from methacrylic acid, methyl methacrylate and a methacrylate ester, comprising the steps:

B1. providing at least one first component selected from methacrylic acid according to the invention, methyl methacrylate according to the invention, a methacrylate ester according to the invention, and a polymer according to the invention comprising at least one monomer unit selected from methacrylic acid, methyl methacrylate and a methacrylate ester, B2. combining the at least one first component provided in B1 with at least one further component.

The at least one further component is preferably at least one component selected from natural or synthetic organic or inorganic polymers, for example selected from a substituted or unsubstituted polystyrene, poly-n-butyl acrylate, a polyacrylonitrile, a polysaccharide, a silica, and a nanomaterial.

The invention also relates to a composition comprising at least one first component selected from methacrylic acid according to the invention, methyl methacrylate according to the invention, a methacrylate ester according to the invention, and a polymer according to the invention comprising at least one monomer unit selected from methacrylic acid, methyl methacrylate and a methacrylate ester and at least one further component, or obtainable according to a process according to the invention.

In the composition according to the invention, the at least one further component is preferably at least one component as described above in connection with the process for producing a composition.

The invention also relates to chemical products such as a shaped article, a moulding material, a film, a sheet, a granulate, a composite, a foam, a fibre, a lubricant, an adhesive, a thickening agent, a suspending agent, a flocculant, a resin, a plastic, a coating, a contact lens, a construction material, an absorbent material, a pharmaceutical, a material for controlled release of active substances, a foam, a fibre, a lubricant, a powder or a particle comprising at least one of methacrylic acid according to the invention, methyl methacrylate according to the invention, methacrylate ester according to the invention, a polymer or co-polymer according to the invention which comprises methacrylic acid, methyl methacrylate, and/or a methacrylate ester, and a composition according to the invention.

The invention also relates to a use of at least one of methacrylic acid according to the invention, methyl methacrylate according to the invention, methacrylate ester according to the invention, a polymer or co-polymer according to the invention which comprises methacrylic acid, methyl methacrylate, and/or a methacrylate ester, and a composition according to the invention, in chemical products such as shaped articles, moulding materials, films, sheets, granulates, composites, adhesives, thickening agents, suspending agents, flocculants, resins, plastics, coatings, contact lenses, construction materials, absorbent materials, pharmaceuticals, materials for controlled release of active substances, foams, fibres, lubricants, powders, particles.

The invention is now illustrated with non-limiting FIGURE and examples.

DESCRIPTION OF THE FIGURE

The FIGURE (FIG. 1) shows schematically a preferred embodiment of the apparatus 1 according to the invention.

A gaseous feed composition comprising at least one of isobutylene, TBA and methacrolein as main component and at least one of methanol, ethanol, dimethyl ether, MTBE, ETBE and formaldehyde as co-compound is provided to the catalytic reaction zone 3 from splitting unit 7 by means of supply 2. The gaseous feed composition may be conducted via conduit unit 6, or conduit unit 6 may be bypassed by the gaseous feed composition by means of bypass 31, depending on the desired constitution of the feed composition. Conduit unit 6 serves to regulate the flow of the feed composition towards catalytic reaction zone 3 and to regulate the constitution of the feed composition. In a preferred embodiment this occurs by separating a part of at least one of methanol, dimethyl ether and formaldehyde by means of means for separation 14. The apparatus 1 can comprise one or more pre-purification units 18 for the respective co-compounds and/or for isobutylene and/or for the feed composition. The feed composition is conducted via supply 2 into the first oxidation area 9 of catalytic reaction zone 3. Each oxidation area 9, 10, is supplied with air, steam and diluent by means of air supply 22, steam supply 23 and diluent supply 30 respectively. Diluent supply 30 is optionally supplied with diluent by means of diluent recycle flow 33 from quench unit 15 and/or purification unit 4, optionally via a combustion unit 34 (recycle flow 33 and combustion unit 34 are not shown for the sake of clarity). In first oxidation unit 8a, comprising first oxidation catalyst 12 (not shown), of first oxidation area 9, the gaseous feed composition is subjected to catalytic gas phase oxidation to form methacrolein as main oxidation product in a first gaseous oxidation phase. The first oxidation phase then flows to second oxidation area 10a of catalytic reaction zone 3, via optional quench area 32. Second oxidation area 10a comprises second oxidation catalyst 13a (not shown) in second oxidation unit 8b. In second oxidation unit 8b the first oxidation phase is subjected to a second catalytic gas phase oxidation to form mainly methacrylic acid as main oxidation product in a second gaseous oxidation phase. Methyl methacrylate is also formed as minor oxidation product in one or both of the oxidation areas 9 and 10a. The second gaseous oxidation phase is then conducted to quench unit 15, where the methacrylic acid is condensed with a quenching agent to form a quench phase comprising methacrylic acid and impurities. Unreacted methacrolein is separated from the quenched second oxidation phase and can be recycled to second oxidation area 10a via methacrolein recycle conduit 24. The quench phase comprising methacrylic acid, methyl methacrylate and impurities is then conducted to purification unit 4, where methacrylic acid and methyl methacrylate are at least partially separated from the quenching agent and from the impurities. Purification unit 4 can include one or more purification stages, 4a, 4b, etc. (not shown in the FIGURE), depending on the desired degree of purity of methacrylic acid. Methacrolein can also be separated in purification unit 4, and can be recycled via methacrolein recycle conduit 24. Purified methacrylic acid which is not intended for esterification can be collected from purification unit 4 via outlet 25. The methacrylic acid to be converted into methyl methacrylate is conducted to esterification unit 5. Esterification unit 5 comprises an esterification catalyst 16. Methanol is supplied to esterification unit 5 by means of methanol supply 17, whereby a methanol purification unit 19 can be located upstream of esterification unit 5. The methanol can be supplied, optionally via methanol purification unit 19, from splitting unit 7 if this is a splitting unit for MTBE, from conduit unit 6, or from a different methanol source (not shown in the FIGURE). In esterification unit 5, the methacrylic acid and the methanol are esterified over esterification catalyst 16 (not shown) to form an esterification phase comprising methyl methacrylate as main esterification product, together with impurities and unreacted starting materials. From esterification unit 5 the esterification phase can be conducted to purification unit 20, where the methyl methacrylate is separated from the reaction composition and from impurities. Purification unit 20 can comprise one or more purification stages 20a, 20b, etc. depending on the desired degree of purity of methyl methacrylate. Methyl methacrylate is recovered from purification unit 20 via outlet 26. Unreacted methanol and/or methacrylic acid present in the esterification phase can also be separated in purification unit 20 and removed from purification unit 20 via methacrylic acid outlet 28 and methanol outlet 29 respectively. One or both of methanol and methacrylic acid can be recycled to esterification unit 5, optionally via methanol purification unit 19 and methacrylic acid purification unit 4 respectively, or one or both can be conducted away.

The catalytic reaction zone 3 illustrated in FIG. 1 as a two-stage oxidation zone can also be considered as a one-stage oxidation zone. In this embodiment, the purified isobutylene phase is conducted to catalytic reaction zone 3, comprising an oxidation area 9. In oxidation area 9, methacrolein is formed and converted continuously to methacrylic acid.

EXAMPLES

Examples 1-3

A feed composition is prepared with composition according to Table 1.

TABLE 1

|  | Example 1 (control) (mol %) | Example 2 (mol %) | Example 3 (mol %) |
|---|---|---|---|
| Isobutylene | 100 | 96.6 | 93.9 |
| Methanol | 0 | 3.4 | 4.7 |

$O_2$, $H_2O$ and diluent gases are added to the feed composition in the molar ratio given in Table 2.

TABLE 2

|  | Mol | Mol % |
|---|---|---|
| IBEN | 1 | 6 |
| $O_2$ | 2 | 13 |
| $N_2$ | 8 | 51 |
| $H_2O$ | 1.8 | 11 |
| $N_2/CO_2$ | 3 | 19 |

The resulting composition is then subjected to a first oxidation reactor, in which IBEN was oxidised to methacrolein according to the process and under the conditions of Example 15 of EP 0 807 465 A1.

To the first oxidation phase resulting from this first oxidation were then added $O_2$, $H_2O$ and diluent gases in molar amounts according to Table 3, based on the number of moles IBEN in the feed composition subjected to the first oxidation reactor.

TABLE 3

|  | Mol | Mol % |
|---|---|---|
| $O_2$ | 1 | 5 |
| $N_2$ | 12 | 59 |
| $H_2O$ | 3.5 | 17 |
| $N_2/CO_2$ | 3 | 15 |

This feed was then subjected to a second oxidation reactor. In this second reactor, methacrolein was oxidised to methacrylic acid according to the process and under the conditions of Example 1 of EP 1 325 780 A1.

Yields of methacrylic acid together with methyl methacrylate were obtained according to Table 4, based on the number of moles of isobutylene introduced into the first oxidation reactor. The yields are given as relative yields, based on the yield of the control (Example 1, with no methanol in the feed composition).

TABLE 4

| Example | Relative yield |
|---|---|
| 1 (control) | 1.00 |
| 2 | 1.022 |
| 3 | 1.034 |

The yields are thus improved compared to the control, by 2.2% and 3.4% for Examples 2 and 3 respectively.

Example 4

The same procedure was followed as for examples 2 and 3, with the difference that the feed composition had composition 97.6 mol % isobutylene and 2.4 mol % dimethyl ether. A separate control was also carried out without dimethyl ether, in order to compare the yields and derive the relative yield.

A relative yield of 1.032 was obtained, i.e. an improvement of 3.2%, compared to the control (with relative yield of 1.00).

Example 5

Preparation of Methyl Methacrylate

One mole of the methacrylic acid obtained in Example 3 was converted to methyl methacrylate by reaction with 1.2 moles technical grade methanol, in a liquid phase reaction in a fixed bed reactor packed with an acidic ion exchange resin as described in EP 1 254 887 A1, with the difference that Amberlyst® (Rohm & Haas Corp.) is used as acidic ion exchange resin. The conversion of methacrylic acid to methyl methacrylate was 45%, based on methacrylic acid.

Example 6

Preparation of N-Butyl Methacrylate n-Butyl methacrylate was prepared according to the process of Example 2 of DE 103 01 007 A1 by transesterification of the methyl methacrylate obtained in Example 5 above.

REFERENCE NUMERALS 1 apparatus
2 supply
3 catalytic reaction zone
4 first purification unit
4a first purification stage
4b further purification stage
5 esterification unit
5 conduit unit
6 splitting unit
7 oxidation unit
8a first oxidation unit
8b second oxidation unit
9 first oxidation area
10 further oxidation area
10a second oxidation area
12 first oxidation catalyst
13 further oxidation catalyst
13a second oxidation catalyst
14 means for separating least a part of the at least one co-compound
15 quench unit
16 esterification catalyst
17 methanol supply
18 pre-purification unit
19 purification unit for methanol
20 purification unit for methyl methacrylate
22 supply for air
23 supply for water
24 methacrolein recycle conduit
25 outlet for methacrylic acid
26 outlet for methyl methacrylate 28 outlet for methacrylic acid
29 outlet for methanol
30 diluent supply
31 bypass
32 quench area
33 diluent recycle flow
34 combustion unit

The invention claimed is:

1. A process comprising:
   at least partially oxidizing a feed composition comprising
   (i) a main compound which is at least isobutylene, and
   (ii) at least one co-compound selected from the group consisting of methanol, dimethyl ether, ethanol, methyl tert-butyl ether, ethyl tert-butyl ether and formaldehyde,
   in a catalytic reaction zone to obtain an oxidation phase comprising methacrylic acid as the main product, and
   optionally, esterifying at least a part of the oxidation phase, wherein
   said process occurs at least partially in the gas phase,
   the feed composition is obtained by splitting of methyl tert-butyl ether or of ethyl tert-butyl ether,
   the oxidation takes place in at least two separate oxidation stages, which comprise a first oxidation to form methacrolein as the main product and a second oxidation to form methacrylic acid as the main product.

2. The process according to claim 1, further comprising:
   esterifying at least a part of said at least one co-compound.

3. The process according to claim 1, wherein the feed composition has a content of not less than 5 ppm of the at least one co-compound.

4. The process according to claim 1, wherein the feed composition comprises the at least one co-compound in a range from 0.0005 to 10 wt. % based on the total weight of main compound and co-compound in the feed composition.

5. The process according to claim 1, wherein the oxidation phase comprises at least 0.0005 wt. % methyl methacrylate, based on the hydrocarbons in the oxidation phase.

6. The process according to claim 2, wherein the at least one part of said at least one co-compound is at least 90 wt. % of the at least one co-compound.

7. The process according to claim 1, wherein said process is performed in an apparatus for production of methacrylic acid, said apparatus comprising:
   i) a supply for a feed composition comprising a main compound which is at least isobutylene, and at least one co-compound selected from the group consisting of: methanol, dimethyl ether, ethanol, methyl tert-butyl ether, ethyl tert-butyl ether and formaldehyde; in fluid communication with
   ii) a catalytic reaction zone for at least partial conversion of the feed composition into methacrylic acid as the main product; in fluid communication with
   iii) optionally, at least one first purification unit.

8. A process for preparation of a methacrylate ester with formula $[CH_2{=}C(CH_3)C({=}O)O]_n{-}R$, comprising:
   α1 preparing methacrylic acid according to the process of claim 1; and
   α3 reacting the methacrylic acid obtained in α1 with an alcohol of formula $R(OH)_m$,
   wherein n and m represent an integer from 1 to 10, and
   R is at least one selected from the group consisting of a linear hydrocarbon, a branched hydrocarbon, a saturated hydrocarbon, an unsaturated hydrocarbon, an aliphatic hydrocarbon, an aromatic hydrocarbon, a ring hydrocarbon, a straight chain hydrocarbon, a linear heteroatom-comprising hydrocarbon, a branched heteroatom-comprising hydrocarbon, a saturated heteroatom-comprising hydrocarbon, an unsaturated heteroatom-comprising hydrocarbon, an aliphatic heteroatom-comprising hydrocarbon, an aromatic heteroatom-comprising hydrocarbon, a ring heteroatom-comprising hydrocarbon, and a straight chain heteroatom-comprising hydrocarbon.

9. A process for producing a polymer comprising at least one monomer unit selected from methacrylic acid, methyl methacrylate and a methacrylic ester with formula $[CH_2{=}C(CH_3)C({=}O)]_n{-}R$, wherein
   n represents an integer from 1 to 10, and
   R is at least one selected from the group consisting of a linear hydrocarbon, a branched hydrocarbon, a saturated hydrocarbon, an unsaturated hydrocarbon, an aliphatic hydrocarbon, an aromatic hydrocarbon, a ring hydrocarbon, a straight chain hydrocarbon, a linear heteroatom-comprising hydrocarbon, a branched heteroatom-comprising hydrocarbon, a saturated heteroatom-comprising hydrocarbon, an unsaturated heteroatom-comprising hydrocarbon, an aliphatic heteroatom-comprising hydrocarbon, an aromatic heteroatom-comprising hydrocarbon, a ring heteroatom-comprising hydrocarbon, and a straight chain heteroatom-comprising hydrocarbon,
   comprising:
   A1. preparing at least one of methacrylic acid according to a process of subjecting a feed composition comprising
   (i) a main compound which is at least isobutylene, and
   (ii) at least one co-compound selected from the group consisting of methanol, dimethyl ether, ethanol, methyl tert-butyl ether, ethyl tert-butyl ether and formaldehyde,
   in a catalytic reaction zone to obtain an oxidation phase comprising methacrylic acid as the main product, methyl methacrylate, and at least one methacrylate ester according to a process according to claim 8,
   A2a. polymerizing at least one of the methacrylic acid, the methyl methacrylate and the at least one methacrylate ester obtained in A1, and
   A2b. optionally polymerizing at least one co-monomer which is co-polymerisable with at least one of methacrylic acid, methyl methacrylate and methacrylate ester.

10. The process according to claim 9, wherein the at least one co-monomer is at least one co-monomer selected from the group consisting of: styrene, butadiene, acrylonitrile, butyl acrylate, vinyl acetate, and methyl acrylate.

11. A process for producing a composition comprising at least a first component selected from methacrylic acid, methyl methacrylate, at least one methacrylate ester, and a polymer comprising at least one monomer unit selected from methacrylic acid, methyl methacrylate and a methacrylate ester, comprising:
   B1. obtaining at least one first component selected from methacrylic acid, methyl methacrylate, a methacrylate ester and a polymer according to the process of claim 9;
   B2. optionally combining the at least one first component obtained in B1 with at least one further component.

12. The process according to claim 11, wherein the at least one further component is at least one component selected from a substituted polystyrene, an unsubstituted polystyrene, a poly-n-butyl acrylate, a polyacrylonitrile, a polysaccharide, a silica and a nanomaterial.

13. The process for preparation of a methacrylate ester according to claim 8, wherein said process for the preparation of methacrylic acid is performed in an apparatus for production of methacrylic acid, said apparatus comprising:

i) a supply for a feed composition comprising a main compound which is at least isobutylene and at least one co-compound selected from the group consisting of methanol, dimethyl ether, ethanol, methyl tert-butyl ether, ethyl tert-butyl ether and formaldehyde; in fluid communication with ii) a catalytic reaction zone for at least partial conversion of the feed composition into methacrylic acid as the main product; in fluid communication with iii) optionally, at least one first purification unit.

14. The process for preparation of a methacrylate ester according to claim 8, wherein said process for the preparation of methyl methacrylate is performed in an apparatus for production of methyl methacrylate, said apparatus comprising:

i) a supply for a feed composition comprising a main compound which is at least isobutylene and at least one co-compound selected from the group consisting of methanol, dimethyl ether, ethanol, methyl tert-butyl ether, ethyl tert-butyl ether and formaldehyde; in fluid communication with ii) a catalytic reaction zone for at least partial conversion of the feed composition into methacrylic acid as the main product; in fluid communication with iii) optionally, at least one first purification unit; in fluid communication with iv) an esterification unit;

optionally, a conduit unit; in fluid communication with at least the supply and the esterification unit.

15. A process for producing a polymer according to claim 9, wherein said process for the preparation of methacrylic acid is performed in an apparatus for production of methacrylic acid, said apparatus comprising:

i) a supply for a feed composition comprising a main compound which is at least isobutylene and at least one co-compound selected from the group consisting of methanol, dimethyl ether, ethanol, methyl tert-butyl ether, ethyl tert-butyl ether and formaldehyde; in fluid communication with ii) a catalytic reaction zone for at least partial conversion of the feed composition into methacrylic acid as the main product; in fluid communication with iii) optionally, at least one first purification unit.

16. A process for producing a polymer according to claim 9, wherein said methyl methacrylate is obtained by the process of:

a) subjecting a feed composition comprising a main compound which is at least isobutylene and at least one co-compound selected from the group consisting of methanol, dimethyl ether, ethanol, methyl tert-butyl ether, ethyl tert-butyl ether and formaldehyde, in the presence of a first part of said at least one co-compound to a catalytic reaction zone and obtaining an oxidation phase comprising methacrylic acid as the main product; and b) esterification of at least a part of the oxidation phase obtained a).

17. A process for producing a polymer according to claim 16, wherein said process for the preparation of methyl methacrylate is performed in an apparatus for production of methyl methacrylate, comprising:

i) a supply for a feed composition comprising a main compound which is at least isobutylene and at least one co-compound selected from the group consisting of methanol, dimethyl ether, ethanol, methyl tert-butyl ether, ethyl tert-butyl ether and formaldehyde; in fluid communication with ii) a catalytic reaction zone for at least partial conversion of the feed composition into methacrylic acid as the main product; in fluid communication with iii) optionally, at least one first purification unit; in fluid communication with iv) an esterification unit;

optionally, a conduit unit; in fluid communication with at least the supply and the esterification unit.

18. A process for producing a composition according to claim 11, wherein the methacrylic acid is obtained by the following process:

subjecting a feed composition comprising a main compound which is at least isobutylene, and at least one co-compound selected from the group consisting of methanol, dimethyl ether, ethanol, methyl tert-butyl ether, ethyl tert-butyl ether and formaldehyde, in the presence of a first part of said at least one co-compound to a catalytic reaction zone and obtaining an oxidation phase comprising methacrylic acid as the main product.

19. A process for producing a composition according to claim 11, wherein the methyl methacrylate is obtained by the following process:

a) subjecting a feed composition comprising a main compound which is at least isobutylene and at least one co-compound selected from the group consisting of methanol, dimethyl ether, ethanol, methyl tert-butyl ether, ethyl tert-butyl ether and formaldehyde, in the presence of a first part of said at least one co-compound to a catalytic reaction zone and obtaining an oxidation phase comprising methacrylic acid as the main product; and b) esterification of at least a part of the oxidation phase obtained a).

20. A process for producing a composition according to claim 11, wherein the methacrylate ester has a formula $[CH_2=C(CH_3)C(=O)]_n$—R, wherein n represents an integer from 1 to 10, and R is at least one selected from the group consisting of a linear hydrocarbon, a branched hydrocarbon, a saturated hydrocarbon, an unsaturated hydrocarbon, an aliphatic hydrocarbon, an aromatic hydrocarbon, a ring hydrocarbon, a straight chain hydrocarbon, a linear heteroatom-comprising hydrocarbon, a branched heteroatom-comprising hydrocarbon, a saturated heteroatom-comprising hydrocarbon, an unsaturated heteroatom-comprising hydrocarbon, an aliphatic heteroatom-comprising hydrocarbon, an aromatic heteroatom-comprising hydrocarbon, a ring heteroatom-comprising hydrocarbon, and a straight chain heteroatom-comprising hydrocarbon.

21. The process of claim 1, wherein the oxidizable compounds of the feed composition consist of the main compound and the co-compound.

* * * * *

UNITED STATES PATENT AND TRADEMARK OFFICE
CERTIFICATE OF CORRECTION

PATENT NO. : 8,829,235 B2  
APPLICATION NO. : 12/598438  
DATED : September 9, 2014  
INVENTOR(S) : Torsten Balduf Page 1 of 1

It is certified that error appears in the above-identified patent and that said Letters Patent is hereby corrected as shown below:

On the title page, Item (73), the Assignee's Information is incorrect. Item (73) should read:

--(73) Assignee: Evonik Röhm GmbH, Darmstadt (DE)--

Signed and Sealed this
Twenty-third Day of December, 2014

Michelle K. Lee
*Deputy Director of the United States Patent and Trademark Office*